United States Patent
Stoffman et al.

(10) Patent No.: US 9,451,986 B2
(45) Date of Patent: Sep. 27, 2016

(54) PERCUTANEOUS SACROILIAC JOINT IMPLANT AND METHOD FOR SURGICALLY INSERTING AND SECURING THE IMPLANT INTO THE SACROILIAC JOINT

(71) Applicant: Michael R. Stoffman, Williamsville, NY (US)

(72) Inventors: Michael R. Stoffman, Williamsville, NY (US); Kristin Campanie, Amherst, NY (US); Craig Dunn, Amherst, NY (US)

(73) Assignee: Michael R. Stoffman, Williamsville, NY (US)

( * ) Notice: Subject to any disclaimer, the term of this patent is extended or adjusted under 35 U.S.C. 154(b) by 280 days.

(21) Appl. No.: 13/749,194

(22) Filed: Jan. 24, 2013

(65) Prior Publication Data
US 2014/0207240 A1    Jul. 24, 2014

(51) Int. Cl.
*A61F 2/30* (2006.01)
*A61B 17/68* (2006.01)
(Continued)

(52) U.S. Cl.
CPC ........... *A61B 17/68* (2013.01); *A61B 17/7055* (2013.01); *A61B 17/864* (2013.01);
(Continued)

(58) Field of Classification Search
CPC ........... A61F 2002/30995; A61F 2002/30754; A61F 2002/30874; A61F 2002/3085; A61F 2002/30787; A61F 2002/30794; A61F 2002/4223; A61B 17/864; A61B 17/8645
USPC .................... 623/21.18, 23.48; 606/310, 319
See application file for complete search history.

(56) References Cited

U.S. PATENT DOCUMENTS 5,534,031 A * 7/1996 Matsuzaki .............. A61F 2/446
                                                    411/166
5,776,197 A * 7/1998 Rabbe .................... A61B 17/70
                                                    606/247
(Continued)

FOREIGN PATENT DOCUMENTS

JP             10043202 A      2/1998

OTHER PUBLICATIONS

Mixter, WJ, Barr JS—"Rupture of the Intervertebral Disc with Involvement of the Spinal Canal"—N Engl J Med 1934; 211; 210-5 (reprinted in the Journal of Neurosurgery, 1964, vol. 21, 74-81).
(Continued)

*Primary Examiner* — Thomas J Sweet
*Assistant Examiner* — Cheryl Miller
(74) *Attorney, Agent, or Firm* — Simpson & Simpson, PLLC

(57) ABSTRACT

An implantable device including a tapered body having a sidewall, an internal cavity, a first end, and a second end, the sidewall including a frusto-conical inner surface extending from the first end to the second end, the first end including a first end opening and the second end including a second end opening, a first side opening extending through the sidewall, a second side opening extending through the sidewall, the second side opening arranged diametrically opposite the first side opening, an external thread arranged helically about a central longitudinal axis of the tapered body, the external thread having a continuously decreasing outer diameter along the tapered body, a first ancillary member operatively arranged to be inserted through the first end opening and then the first or second side opening, and a second ancillary member operatively arranged to be inserted through the first end opening and then the first or second side opening.

19 Claims, 9 Drawing Sheets

(51) Int. Cl.
*A61B 17/70* (2006.01)
*A61B 17/86* (2006.01)
*A61B 17/56* (2006.01)

(52) U.S. Cl.
CPC ...... *A61B17/8645* (2013.01); *A61B 2017/561* (2013.01); *A61F 2002/30736* (2013.01); *A61F 2002/30754* (2013.01); *A61F 2002/30794* (2013.01); *A61F 2002/30874* (2013.01); *A61F 2002/30995* (2013.01)

(56) References Cited

U.S. PATENT DOCUMENTS

| | | | |
|---|---|---|---|
| 6,022,350 | A | 2/2000 | Ganem |
| 6,290,703 | B1 | 9/2001 | Ganem |
| 6,558,423 | B1 | 5/2003 | Michelson |
| 6,849,093 | B2 | 2/2005 | Michelson |
| 6,887,275 | B2 | 5/2005 | Carchidi et al. |
| 7,033,394 | B2 | 4/2006 | Michelson |
| 7,041,135 | B2 | 5/2006 | Michelson |
| 7,094,239 | B1 | 8/2006 | Michelson |
| 7,291,149 | B1* | 11/2007 | Michelson ............... 606/86 A |
| 7,326,248 | B2 | 2/2008 | Michelson |
| 7,637,951 | B2 | 12/2009 | Michelson |
| 7,637,954 | B2 | 12/2009 | Michelson |
| 7,931,840 | B2 | 4/2011 | Michelson |
| 8,142,503 | B2 | 3/2012 | Malone |
| 8,808,377 | B2* | 8/2014 | Donner ..................... 623/17.11 |
| 9,060,820 | B2* | 6/2015 | Nelson ............... A61B 17/7208 |
| 2001/0005796 | A1* | 6/2001 | Zdeblick et al. ........... 623/17.11 |
| 2002/0156478 | A1* | 10/2002 | Bonutti ......................... 606/86 |
| 2003/0088251 | A1* | 5/2003 | Braun ............... A61B 17/7022 |
| | | | 606/263 |
| 2003/0199983 | A1* | 10/2003 | Michelson ......... A61B 17/7059 |
| | | | 623/17.16 |
| 2004/0147929 | A1 | 7/2004 | Biedermann et al. |
| 2004/0220673 | A1* | 11/2004 | Pria ....................... A61F 2/4081 |
| | | | 623/19.12 |
| 2005/0096658 | A1 | 5/2005 | Carchidi et al. |
| 2005/0216082 | A1* | 9/2005 | Wilson et al. ............. 623/17.11 |
| 2006/0206208 | A1 | 9/2006 | Michelson |
| 2007/0299445 | A1 | 12/2007 | Shadduck et al. |
| 2009/0024174 | A1* | 1/2009 | Stark ........................... 606/321 |
| 2010/0131011 | A1 | 5/2010 | Stark |
| 2010/0145463 | A1 | 6/2010 | Michelson |
| 2010/0312280 | A1 | 12/2010 | Overes et al. |
| 2011/0125267 | A1 | 5/2011 | Michelson |
| 2011/0230884 | A1 | 9/2011 | Mantzaris et al. |
| 2013/0053902 | A1* | 2/2013 | Trudeau ....................... 606/313 |
| 2013/0211522 | A1* | 8/2013 | Weiss ........................ A61F 2/28 |
| | | | 623/16.11 |
| 2013/0304224 | A1* | 11/2013 | Schmidt et al. ........... 623/21.18 |

OTHER PUBLICATIONS

Cohen, Steven P. MD—"Sacroiliac Joint Pain: A Comprehensive Review of Anatomy, Diagnosis and Treatment"—Anesth Analg 2005;101:1440-53—2005 by the International Anesthesia Research Society; 0003-2999/05.

Wise, Christopher L. MD and Dall, Bruce E. MD—"Minimally Invasive Sacroiliac Arthrodesis—Outcomes of a New Technique"—J Spinal Disord Tech, vol. 21, No. 8, Dec. 2008.

Al-Khayer, Ahmad, MRCS, Hegarty, Jim, Hahn, David, FRCS (Tr&Orth), and Grevitt, Michael Paul, FRCS (Tr&Orth)—"Percutaneous Sacroiliac Joint Arthrodesis: A Novel Technique"—J Spinal Disord Tech, vol. 21, No. 5, Jul. 2008.

* cited by examiner

PERCUTANEOUS SACROILIAC JOINT IMPLANT AND METHOD FOR SURGICALLY INSERTING AND SECURING THE IMPLANT INTO THE SACROILIAC JOINT

FIELD OF THE INVENTION

The present disclosure broadly relates to medical devices for the treatment of musculoskeletal disorders and, more particularly, to surgical implantable devices, which facilitate bone growth. Even more particularly, the invention relates to a percutaneous surgical implant, which is secured to the sacroiliac joint, and a method for inserting and securing the same.

BACKGROUND OF THE INVENTION

Sacroiliac (SI) joints are formed by the connection of the sacrum to the ilium bones of the pelvis. There are two SI joints in the human body; one on the left and right sides, respectively of the lower spine. Sacroiliac joints are diarthrodial, meaning they allow motion between the bones they connect. Additionally, SI joints are weight bearing, meaning a primary function of the joint is to absorb shock and provide just enough motion and flexibility to lessen stress on the pelvis and spine. In women, the SI joints are weaker, in part, probably, because the SI joints relax during the end stages of parturition, or childbirth. The joints can become painful for a number of reasons including, but not limited to, arthritis, abnormal leg alignment, pregnancy leading to increased stress on the joints, or any condition which alters the normal walking pattern and/or stresses the joints including trauma, infection, cancer, and spinal instability. In the early 1900's the exact causes of back pain were unknown but, there were a number of possible causes including dysfunction of the SI joint. In 1934, Mixter and Barr proclaimed that back pain could result from a posterior rupture of an intervertebral disc. Mixter W J, Barr J S. "*Rupture of the intervertebral disc with involvement of the spinal canal.*" N Engl J Med 1934; 211:210-5. Due to Mixter and Barr's paper, physicians began to consider degenerative disk disease and disk herniation as the primary causes of back pain over SI joint dysfunction. Today, it is believed that approximately 20% of low back pain is SI joint related. There are a number of misdiagnoses of back pain due to the variety of possible causes.

SI joint pain can be treated non-surgically and surgically. One nonsurgical option for pain relief involves the injection of a corticosteroid into the joint, which reduces inflammation of the joint. Another nonsurgical option for pain relief is the use of oral anti-inflammatory medications such as non-steroidal anti-inflammatory drugs (NSAIDS), ibuprofen, and naproxen to reduce inflammation of the painful joint. Physical therapy, yoga, and Pilates can also help relieve pain associated with the SI joint because pain can result from excessive or insufficient motion in the joint. Some patients benefit from wearing a special brace called a sacroiliac belt, which wraps around the hips to hold the SI joint tightly together. This belt can help decrease inflammation of the SI joint.

If non-surgical treatments fail to treat the pain associated with the SI joint, the pain can also be treated surgically by fusing the joint(s). This surgical fusion is also known as arthrodesis. In this surgery, the cartilage covering the surfaces of the SI joints is removed and the bones are held together with plates and screws until they grow together, or fuse. Percutaneous sacroiliac joint fusion is a minimally invasive approach in which cages or screws are placed, with or without bone graft, to achieve a fusion. Smooth or threaded metallic bone fastener devices have been used to achieve a fusion and such devices include a series of metallic, porous plasma spray coated rods, which are surgically inserted across the SI joint. Other systems use cannulated screws.

One surgical implant of the cannulated screw type, found in U.S. Pat. No. 8,142,503 (Malone), has been developed, which comprises a conical hollow facet for facilitating bone growth or repair. The conical hollow facet further comprises threading for facilitating securement to bone, a port to accommodate an allen wrench, an internal cavity for bone morphogenic protein, and a plurality of orifices for facilitating delivery of the substance within the cavity to adjacent bony structures. The facet disclosed also includes a member, which seals the hollow cavity to prevent desired substances from escaping from within the cavity. This reference fails to disclose an open-ended surgical implant having apertures for ancillary screws.

Another surgical implant is disclosed in the Michelson family of patents (U.S. Pat. No. 6,558,423; U.S. Pat. No. 7,033,394; U.S. Pat. No. 7,041,135). The implant disclosed in the Michelson family of patents comprises a cylindrical perforated hollow body having a leading end and a trailing end, holes for the growth of bone and vascular access, and a constant diameter of the screw threading along the length of the cage. The trailing end of the implant further comprises holes to receive a bone screw such that the bone screw would be directed first through the trailing end and then through either one of upper or lower vertebral bone engaging surfaces of the implant and finally into the vertebral body at an angle. This reference fails to disclose a percutaneous sacroiliac joint fusion implant, which comprises an open-ended tapered screw arranged to receive at least two ancillary screws, which can be tapped to determine the trajectory of the ancillary screws while the ancillary screws are engaged with the tapered screw.

United States Patent Application Publication No. 2004/0147929 (Biedermann et al.) discloses yet another surgical implant which comprises a middle conical bone-threading section tapering towards an end and apertures therein which allow for the growing-in of bone material or vessels. This reference fails to disclose an open-ended surgical implant having apertures for ancillary screws.

United States Patent Application Publication No. 2011/0230884 (Mantzaris et al.) discloses a polyaxial screw device to be inserted into a bone structure comprising a tapered screw member, which is cylindrical and has a substantially smooth exterior surface, a threaded portion, and tapered apertures to accommodate lag screws. This reference fails to disclose an open-ended surgical implant having apertures for bone fusion promoting substances and apertures for ancillary screws.

Despite these attempts, surgical treatment of the SI joint has still been problematic because the joint is very deeply located in a region of the human body. Percutaneous surgical implants used on the SI joint have a high rate of screw malpositions, which may be associated with risk of neurologic damage or inefficient stability. Additionally, over time if the SI joint does not completely immobilize because of a percutaneous surgical implant, the spine can shift, the implants can loosen, and pain can result again. Thus, a need has existed for an accurate and effective surgical implant for the fusion of the SI joint.

BRIEF SUMMARY OF THE INVENTION

The present invention comprises an implantable device comprising a tapered body having a sidewall, an internal cavity, a first end, and a second end, the sidewall comprising a single continuous frusto-conical inner surface extending from the first end to the second end, the first end comprising a first end opening defined by the single continuous frusto-conical inner surface and the second end opening comprising a second end opening defined by the single continuous frusto-conical inner surface, a first side opening extending through the sidewall, a second side opening extending through the sidewall, the second side opening arranged diametrically opposite the first side opening, an external thread arranged helically about a central longitudinal axis of the tapered body, the external thread having a continuously decreasing outer diameter along the tapered body, a first ancillary member operatively arranged to be inserted through the first end opening and then the first or second side opening, and a second ancillary member operatively arranged to be inserted through the first end opening and then the first or second side opening. The invention also includes a method for surgically inserting and securing the implant into the sacroiliac joint, comprising the following steps: drilling a tapered body into the sacroiliac joint, tapping and placing a first ancillary member to either the sacrum or the iliac bone through an open end of the tapered body and through a first opening within the tapered body, and tapping and placing a second ancillary member to either the sacrum or the iliac bone through the open end of the body and through a second opening within the body. The implant provides a number of significant improvements to the techniques already available, among which include a single incision approach to percutaneous fusion of the sacroiliac joint while covering greater surface area of the joint; allowing for a deliverable approach and a visible approach to the fusion process; and, tools to decorticate the joint to allow fusion to occur.

The present invention broadly includes an implantable device including a tapered body having a sidewall, an internal cavity, a first end, and a second end, the sidewall including a frusto-conical inner surface extending from the first end to the second end, the first end including a first end opening defined by the frusto-conical inner surface and the second end including a second end opening defined by the frusto-conical inner surface, a first side opening extending through the sidewall, a second side opening extending through the sidewall, the second side opening arranged diametrically opposite the first side opening, an external thread arranged helically about a circumference of the tapered body, the external thread having a continuously decreasing outer diameter along the tapered body, a first ancillary member operatively arranged to extend through and project outwardly through only the first end opening and the first side opening and a second ancillary member operatively arranged to extend through and project outwardly through only the first end opening and the second side opening.

The present invention broadly includes a method for inserting and securing an implantable device into a sacroiliac joint of a person, the method including the following steps: making an incision into the sacroiliac joint, inserting a tapered body into the sacroiliac joint, the tapered body including: a sidewall having a frusto-conical inner surface, an internal cavity, a first end having a first end opening, a second end having a second end opening, a first side opening extending through the sidewall, a second side opening extending through the sidewall, the second side opening arranged diametrically opposite the first side opening, an external thread arranged helically about a circumference of the tapered body, the external thread having a continuously decreasing outer diameter along the tapered body, where the frusto-conical inner surface extends from the first end to the second end and the first end opening defined by the frusto-conical inner surface and the second end opening defined by the frusto-conical inner surface, inserting a first ancillary member into and through only the first end opening and the first side opening and securing the first ancillary member to either a sacrum or an iliac bone and inserting a second ancillary member into and through only the first end opening and the second side opening and securing the second ancillary member to either the sacrum or the iliac bone.

The present invention broadly includes an implantable device, including a body having a sidewall, an internal cavity, a first end, and a second end, the sidewall comprising an inner surface extending between the first end and the second end, the first end including one and only one opening defined by the inner surface and the second end including one and only one opening defined by the inner surface, a first side opening extending through the sidewall, a second side opening extending through the sidewall, an external thread arranged about a circumference of the body, a first ancillary member operatively arranged to extend through and project outwardly through only the one and only one opening of the first end and the first side opening and a second ancillary member operatively arranged to extend through and project outwardly through only the one and only one opening of the first end and the second side opening.

A primary object of the present invention is to provide a safe, accurate, reliable, and minimally invasive method and apparatus for a percutaneous sacroiliac joint fusion.

A further object of the present invention is to provide a safe surgical implant for a percutaneous sacroiliac joint fusion, which allows a surgeon to accurately and effectively secure, with flexibility, a fusion-facilitating device.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention in view of the accompanying drawing figures.

DETAILED DESCRIPTION OF THE INVENTION

At the outset, it should be appreciated that like drawing numbers on different drawing views identify identical, or functionally similar, structural root elements of the invention. Moreover, although any methods, devices or materials similar or equivalent to those described herein can be used in the practice or testing of these embodiments, some embodiments of methods, devices, and materials are now described.

Furthermore, it is understood that this invention is not limited to the particular methodology, materials and modifications described and, as such, may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. It should be appreciated that the term "substantially" is synonymous with terms such as "nearly", "very nearly", "about", "approximately", "around", "bordering on", "close to", "essentially", "in the neighborhood of", "in the vicinity of", etc., and such terms may be used interchangeably as appearing in the specification and claims. The terms "right" and "left" as they refer to the joints and bones refer to the anatomical right and left as opposed to the right and left from the perspective of a viewer of the patent drawings. Although any methods, devices or materials similar or equivalent to those described herein can be used in the practice or testing of the invention, the preferred methods, devices, and materials are now described.

The device of the present invention can be made of titanium, alloys of titanium, carbon fiber, bone or ceramic, Polyetheretherketone (hereinafter referred to as "PEEK"), or any material suitable to be tolerated or bio-absorbable by the human body. Additionally, the device may comprise a unitary structure or may be of a multi-piece construction.

Furthermore, it should be appreciated that although preferred embodiment of the present invention takes the form of a percutaneous sacroiliac joint fusion device, the present invention may also take the form of spinal fusion devices, joint stabilizers, bone fixation devices and other orthopedic appliances where bone-to-bone growth or bone-to-bone stabilization is desired.

Structure

Figure 1:
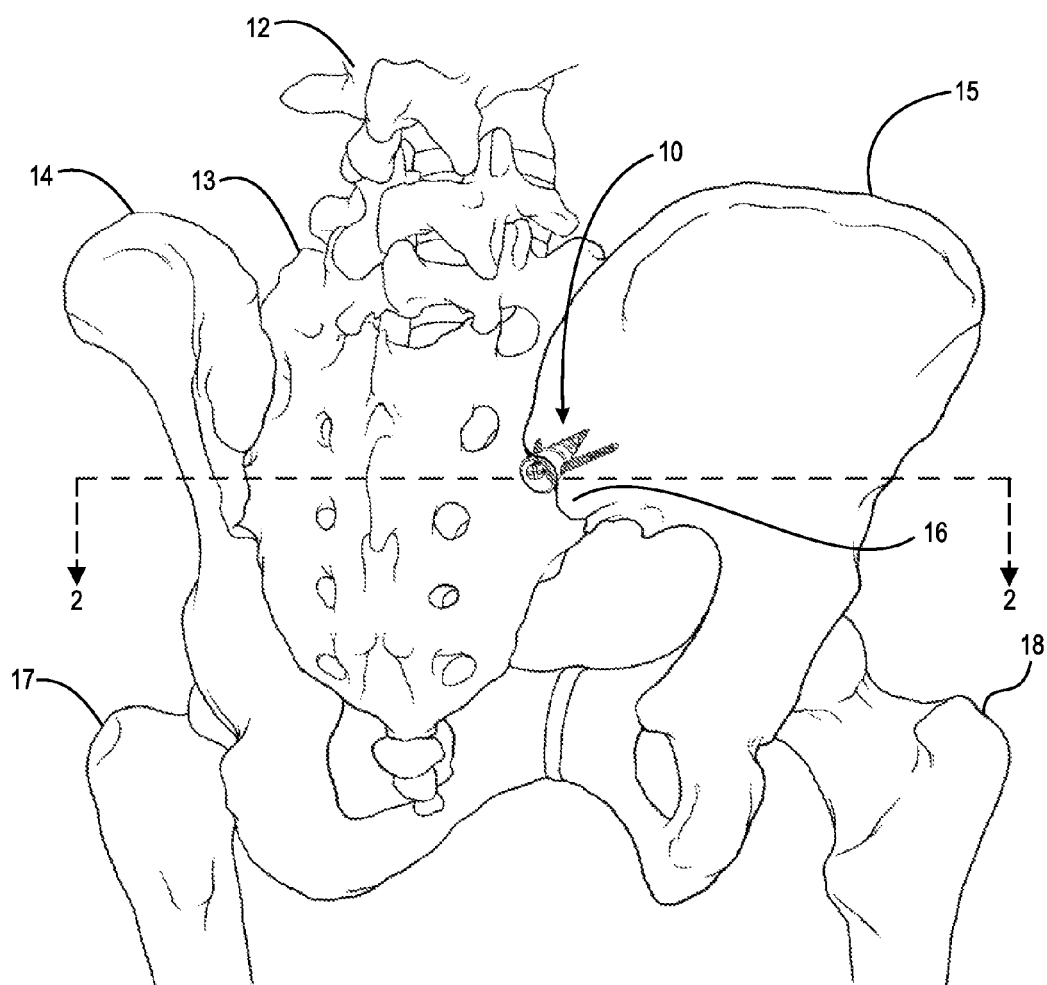
FIG. 1 is a rear perspective view of part of the human skeletal system showing the present invention placed in the SI joint.

Adverting now to the figures, FIG. 1 shows percutaneous sacroiliac joint fusion device 10 (hereinafter SI joint fusion device 10) of the present invention placed within a partial musculoskeletal representation of the mid-portion of a human. Spine 12 is connected to sacrum 13 and sacrum 13 is arranged between left and right ilium bones 14 and 15, respectively. Left ilium bone 14 is adjacent sacrum 13 to the left of sacrum 13. Right ilium bone 15 is adjacent sacrum 13 to the right of sacrum 13. Left and right femurs 17 and 18 protrude downwardly from the pelvis. Sacroiliac joint 16 (hereinafter SI joint 16) is located between right ilium bone 15 and sacrum 13. It should be appreciated that there is another sacroiliac joint located between left ilium bone 14 and sacrum 13 but, for purposes of illustration, we refer to the right sacroiliac joint herein. SI joint fusion device 10 of the present invention could be used on either the right or the left sacroiliac joints.

Figure 2:
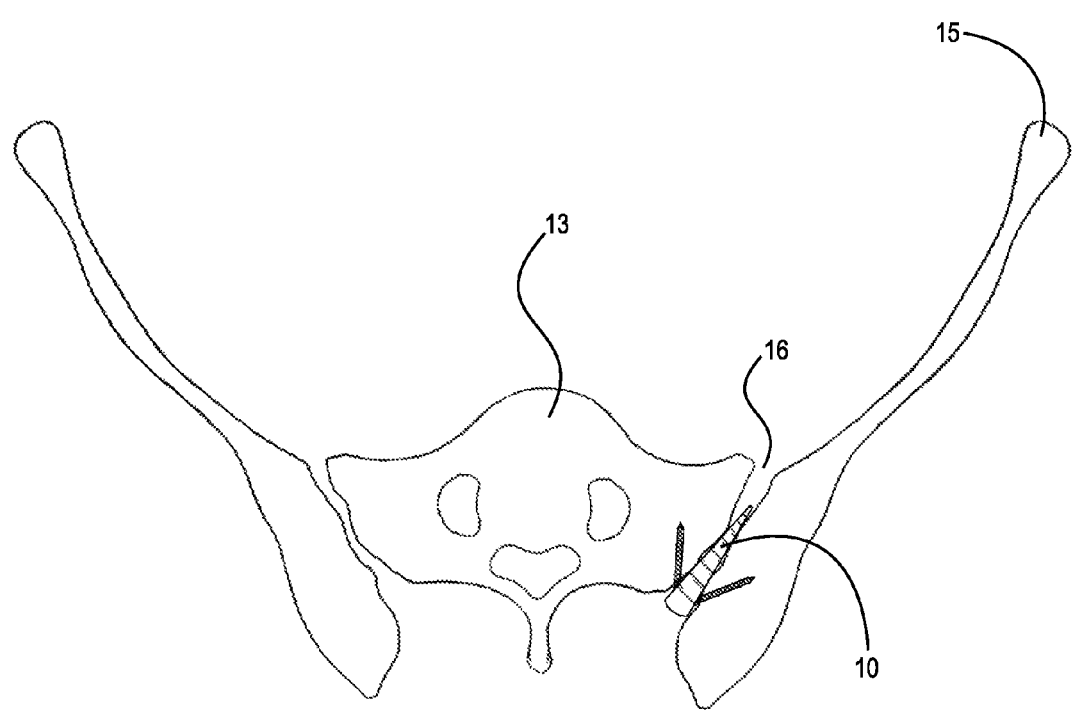
FIG. 2 is a top plan view of the present invention taken along line 2-2 in FIG. 1, with parts of the human skeletal system removed to better illustrate the invention.

FIG. 2 shows a top plan view of SI joint fusion device 10 with parts of the body removed along line 2-2 in FIG. 1 to better illustrate the invention. From this view, it is apparent that SI joint 16 is difficult to access for purposes of a percutaneous SI joint fusion. Additionally, it is apparent that the dimensions of SI joint fusion device 10 depend on the length, width and curvature of each SI joint 16 operated upon. Depending upon these parameters, SI joint fusion device 10 may be secured more toward the incision or more toward the end opposite the incision.

Figure 3:
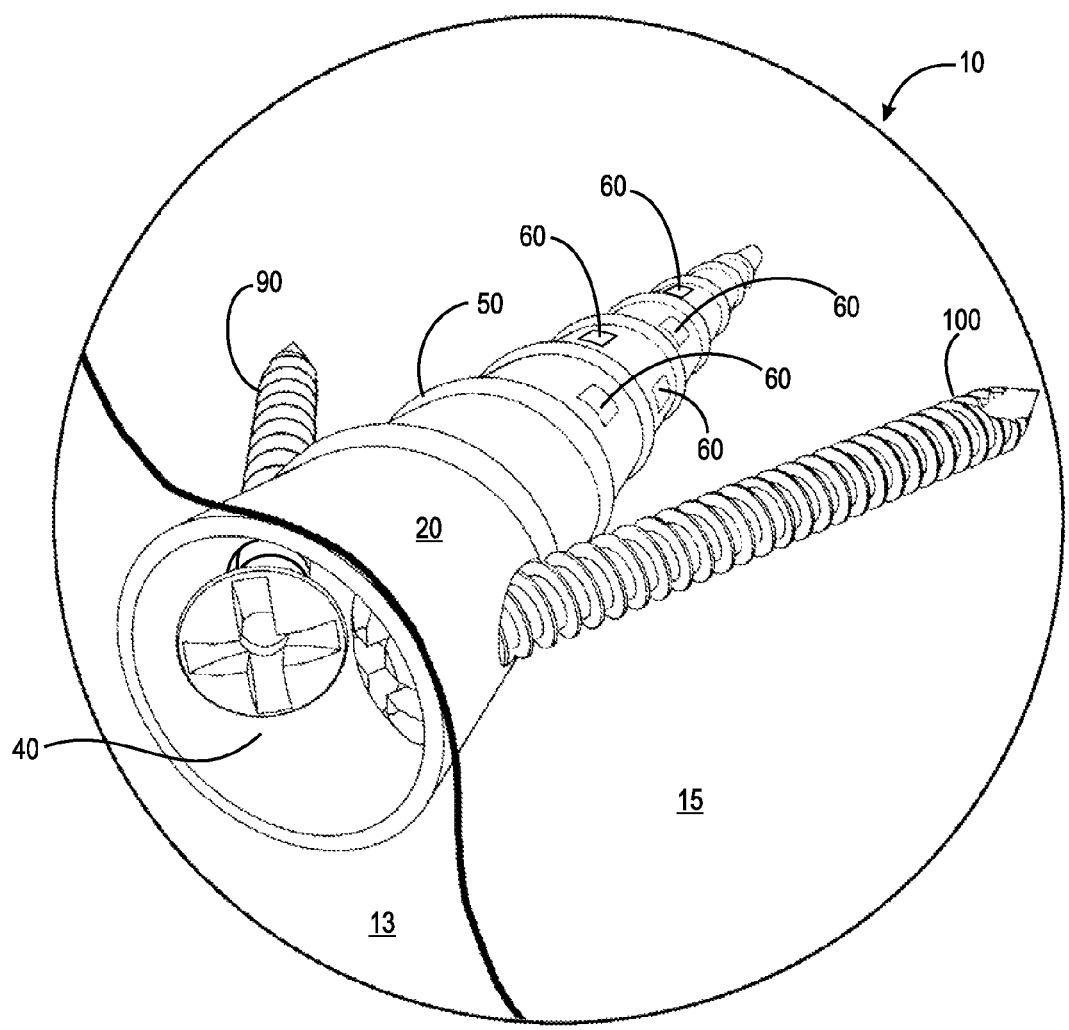
FIG. 3 is a detailed view of the present invention as shown in FIG. 1.

SI joint fusion device 10 of the present invention is shown in FIG. 3, and broadly comprises body 20 and first and second ancillary members 90 and 100, respectively, protruding outwardly from body 20. In the preferred embodiment, body 20 is tapered and frusto-conical. However, it should be appreciated that body 20 could be another shape to accommodate SI joint 16. For example, body 20 could be a non-tapered cone, a cylinder, a tapered cylinder, or a square-based or triangular-based pyramid. Body 20 further comprises first and second apertures 70 and 80, (detailed below) which receive first and second ancillary members 90 and 100, respectively. In the preferred embodiment, body 20 has a width in the range of approximately 3.5 mm-4.5 mm. However, it should be appreciated that body 20 can be manufactured to have a smaller or larger width to accommodate smaller or larger SI joints 16. Additionally, in the preferred embodiment, body 20 is less than 3 cm in length. Similarly, body 20 can be manufactured to have a longer length. First and second ancillary members 90 and 100 pass through first and second apertures 70 and 80, respectively, through end 40 of body 20. Body 20 further comprises threading 50 to help secure SI joint fusion device 10 between sacrum 13 and right ilium bone 15. In the preferred embodiment, threading 50 is helical. However, it should be appreciated, that threading 50 could take any form and need not be continuous. For example, threading 50 could be segmented or threading 50 could comprise a plurality of protrusions. Additionally, body 20 comprises plurality of openings 60 through which fusion-facilitating substances can pass.

Figure 4:
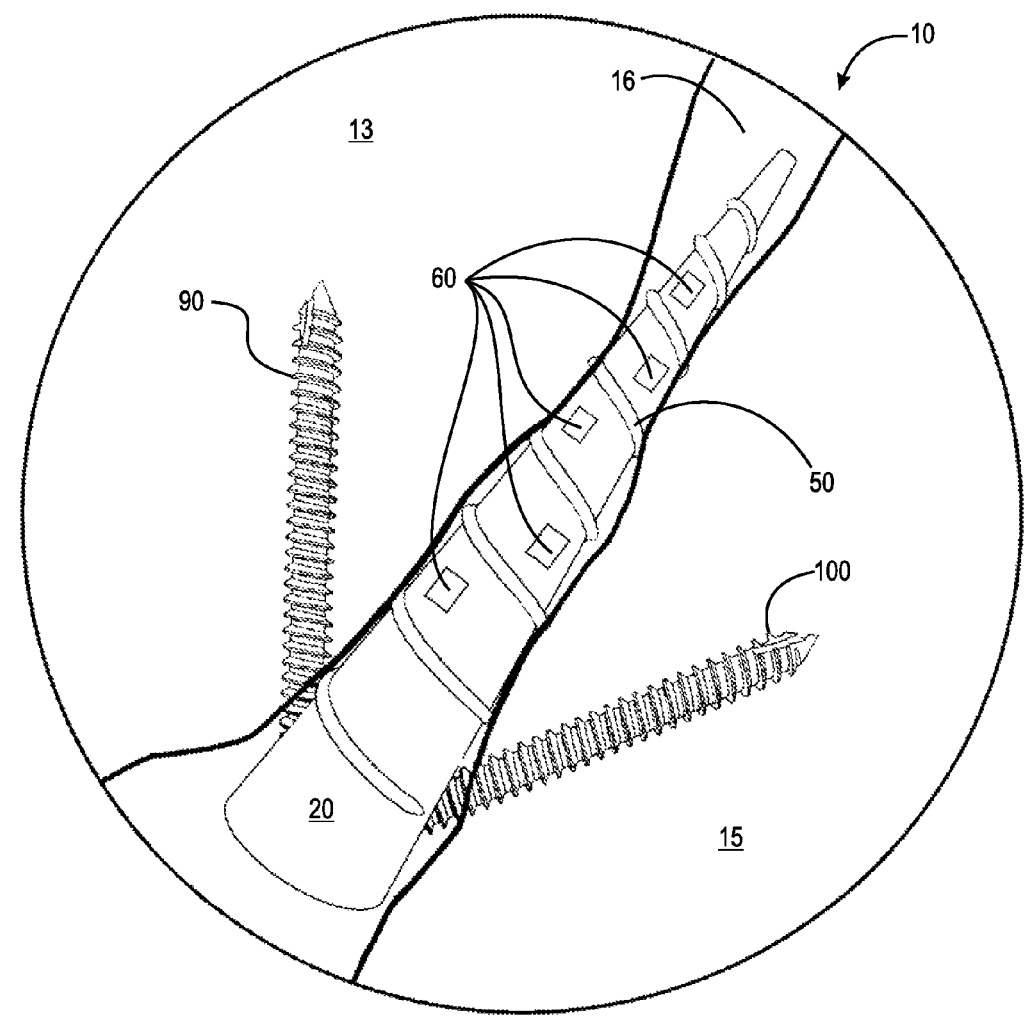
FIG. 4 is a detailed view of the present invention as shown in FIG. 2 as the device would appear secured within the SI joint.

FIG. 4 is a detailed view of SI joint fusion device 10 as pictured in FIG. 2. From this view, body 20 is shown having a taper and a frusto-conical shape. Additionally, threading 50 has a helical shape. The depth of threading 50 can be constant or it can vary. For example, the depth of threading 50 can taper along with the taper of body 20. Alternatively, the depth of threading 50 can taper in a direction opposite to the taper of body 20. In the preferred embodiment, the depth of threading 50 tapers along with the taper of body 20. These tapers are effective in fusing the SI joint 16 because typically, SI joint 16 narrows. Additionally, it should be appreciated that threading 50 could be sharp, rounded, or square. First ancillary member 90 is secured within sacrum 13 and second ancillary member 100 is secured within right ilium bone 15.

In the preferred embodiment, SI joint fusion device 10 is made of PEEK. Nevertheless, it should be appreciated that SI joint fusion device 10 could be made of any suitable material which is highly resistant to thermal degradation and attack by organic and aqueous environments. For example, polytetrafluoroethylene (PTFE) could be an alternative. In the art, PEEK is routinely used for medical implants.

Figure 5:
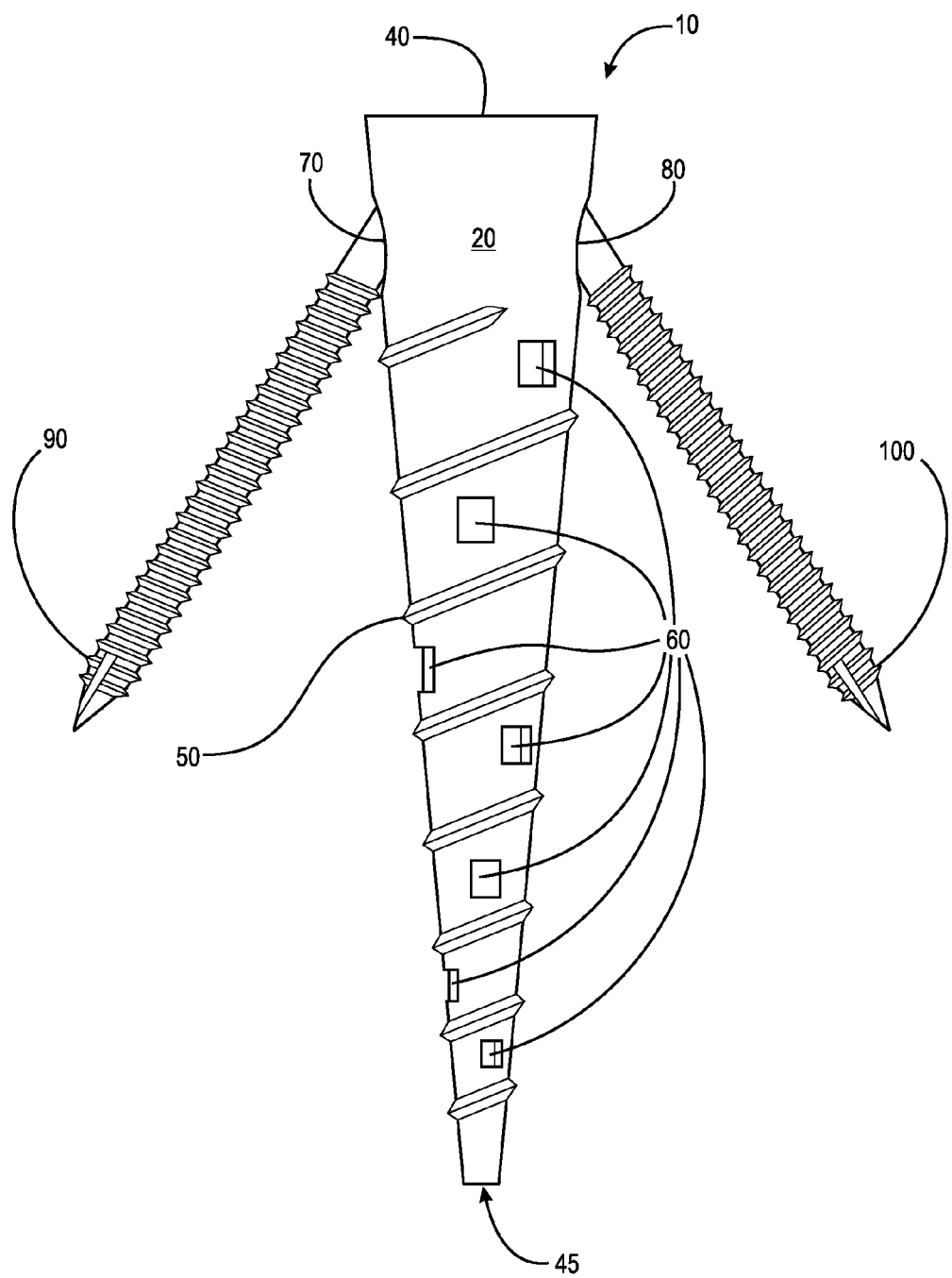
FIG. 5 is a front view of the present invention.

Body 20 is open at both ends and includes end 40 and end 45. As shown in FIG. 5, end 40 is disposed at the top end and end 45 is disposed at the bottom end. Body 20 further includes a sidewall extending between end 40 and end 45. First and second ancillary members 90 and 100, respectively, are arranged to extend through body 20. In an example embodiment, the sidewall of body 20 includes an inner surface extending from end 40 to end 45; the inner surface of the sidewall may be frusto-conical. In an example embodiment, end 40 is parallel to end 45 and both are planar. In an example embodiment, end 40 includes an opening defined by the inner surface of the sidewall of body 20 and end 45 includes an opening defined by the inner surface of the sidewall of body 20. In an example embodiment, end 40 and end 45 each includes only a single opening defined by the inner surface of the sidewall of body 20. In alternate embodiments, these ends could be angled, curved, or segmented. Additionally, end 45 has a smaller diameter than end 40. End 45 can be of any diameter so long as a Kirschner wire or a k-wire substitute can pass through end 45 and end 45 can be arranged within SI joint 16. First and second ancillary members 90 and 100 are arranged to protrude outwardly from body 20 through first and second apertures 70 and 80, respectively. First and second apertures 70 and 80 are arranged within the sidewall of body 20. When first and second ancillary members 90 and 100 are placed through first and second apertures 70 and 80, respectively, the heads of first and second ancillary members 90 and 100 are hidden within body 20. In the preferred embodiment, SI joint fusion device 10 has two apertures 70 and 80 but, in an alternate embodiment, the device could have additional apertures. Additionally, in the preferred embodiment, first aperture 70 is arranged diametrically opposite second aperture 80, and proximate open end 40. However, apertures 70 and 80 could be arranged at other points around and along body 20.

Figure 6:
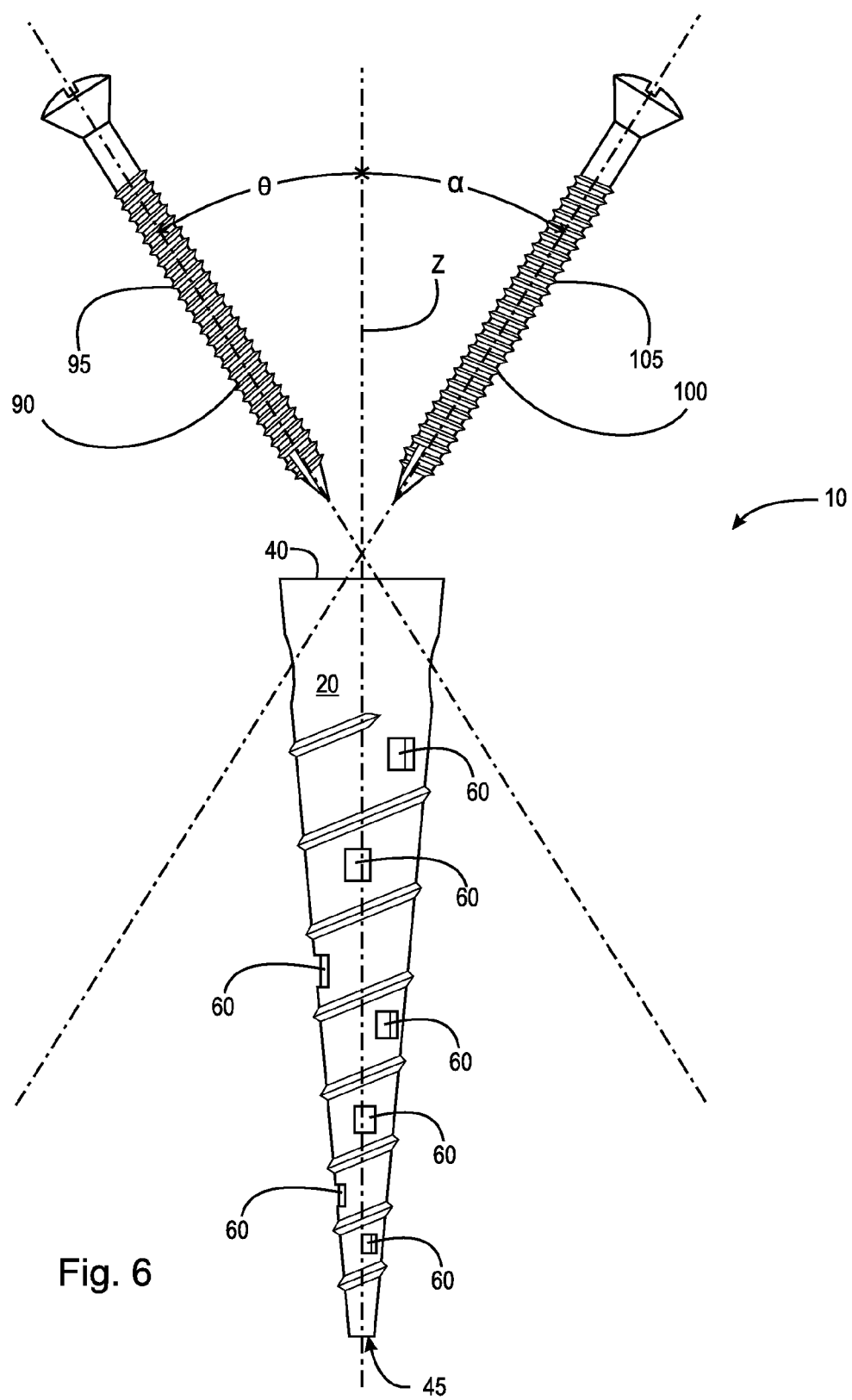
FIG. 6 is an exploded view of the present invention shown in FIG. 5.

FIG. 6 shows the present invention with first and second ancillary members 90 and 100 suspended above body 20. First and second ancillary members 90 and 100 are typical screws such as, preferably, a Phillips oval head. However, first and second ancillary members 90 and 100 could be a Phillips flat head, a Phillips pan head, a Phillips truss head, a slotted flat, oval, pan, truss head, or any other screw suitable for the present invention. Additionally, first and second ancillary members 90 and 100 are self-tapping screws. In the preferred embodiment, first and second ancillary members 90 and 100 feature threading 95 and 105. In the preferred embodiment, threading 95 and 105 are single starts, meaning that there is only one ridge wrapped around the cylinders. However, threading 95 and 105 can be double starts, meaning that there are two ridges wrapped around the cylinders of the screws. Similarly, threading 50 is a single start but, it could be a double start. Along these lines, in alternate embodiments, threading 50, 95 and 105 can be coarse or fine. Alternatively, first and second ancillary members 90 and 100 could have no threading at all and have some other secure means such as, a rod or a pin. Notably, first and second ancillary members 90 and 100 are not coupled to body 20 both when they are engaged and when they are not engaged with body 20. This uncoupled state allows a surgeon greater leeway in determining and setting the screw trajectory.

First and second ancillary members 90 and 100 are arranged above body 20 at angles α and θ in relation to vertical line Z, which is the longitudinal center line of SI joint fusion device 10. Preferably, angles α and θ are both within the range of approximately 10 degrees to 80 degrees. However, it should be appreciated that angles α and θ could be any suitable angle so long as the angle ensures an effective securement between SI joint 16 and sacrum 13 and right ilium bone 15.

Figure 7A:
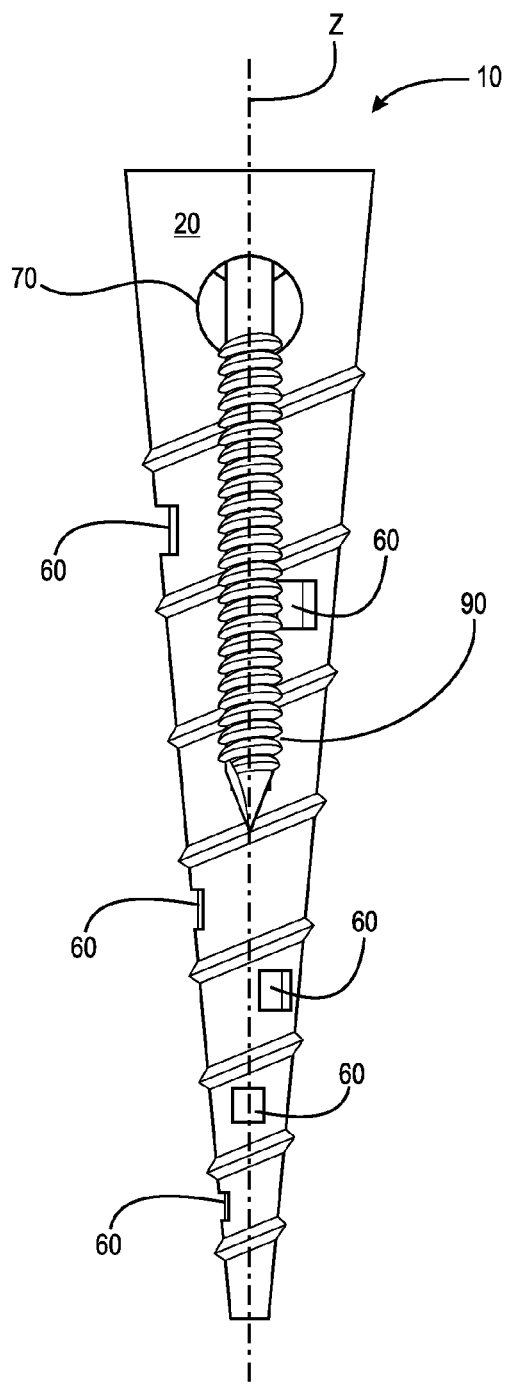
FIG. 7a is a left side view of the present invention as viewed from the left in FIG. 5.
Figure 7B:
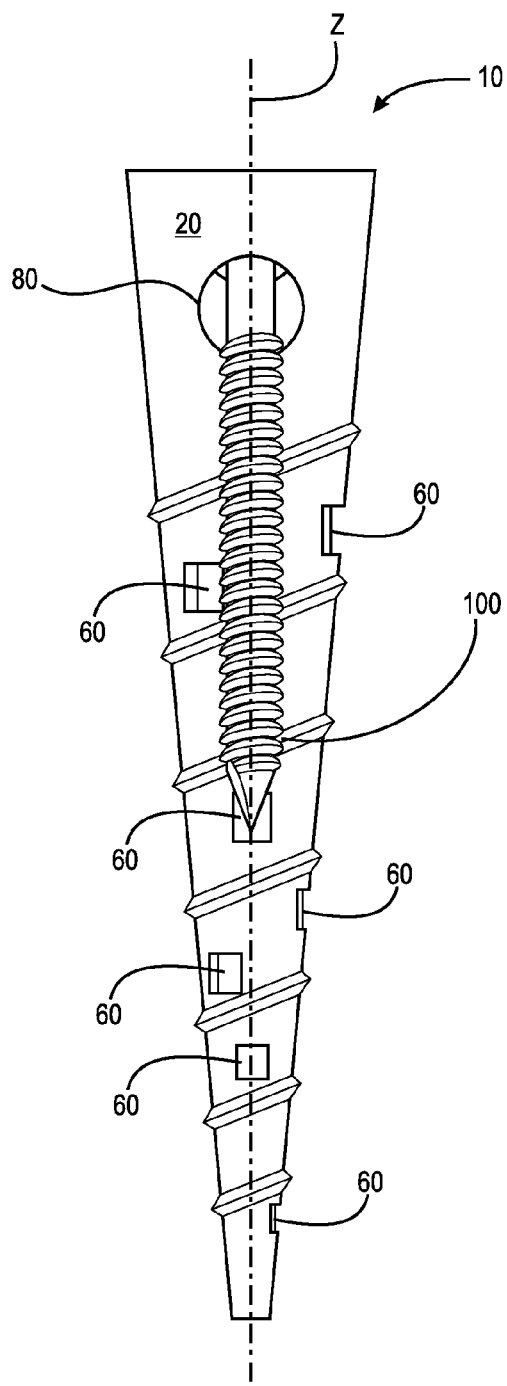
FIG. 7b is a right side view of the present invention as viewed from the right in FIG. 5.

FIG. 7a shows the left side of the present invention shown in FIG. 5 and FIG. 7b shows the right side of the present invention shown in FIG. 5. In FIG. 7a, first ancillary member 90 protrudes from first aperture 70, which is circular. In FIG. 7b, second ancillary member 100 protrudes from second aperture 80, which is circular. The diameters of first and second apertures 70 and 80 are larger than the diameters of first and second ancillary members 90 and 100 to accommodate the passage of members 90 and 100. However, the head portions of first and second ancillary members 90 and 100 are arranged to abut the inner circumferential surfaces of first and second apertures 70 and 80, respectively, such that they do not pass through. Apertures 70 and 80 could be any size or shape to accommodate first and second ancillary members 90 and 100 so that a surgeon can anchor first and second ancillary members 90 and 100 through apertures 70 and 80, respectively, to bone while still engaging first and second ancillary members 90 and 100 with body 20. Apertures 70 and 80 can guide first and second ancillary members 90 and 100, respectively. However, a surgeon also has a tap available to determine the screw trajectory of first and second ancillary members 90 and 100.

Figure 8:
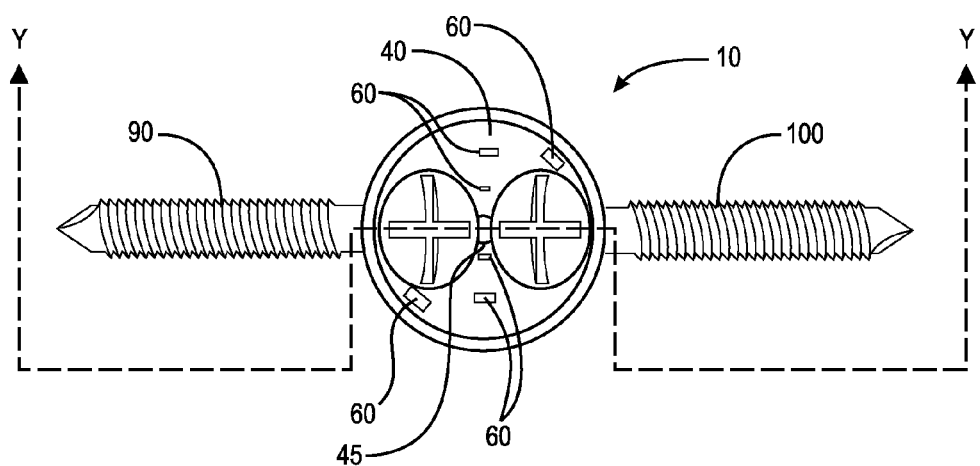
FIG. 8 is a top plan view of the present invention.

End 40 of SI joint fusion device 10 is visible in FIG. 8. Additionally, first and second ancillary members 90 and 100 are visible protruding from underneath end 40 in an outward direction from body 20. End 45 is arranged approximately at the center of end 40 at the opposite end of body 20. In the preferred embodiment, end 40 is circular. Thus, end 45 is arranged at the origin, or center, of end 40 at the opposite end of body 20. In an alternate embodiment, end 45 can be arranged off center of end 40. Similarly, in an alternate embodiment, end 40 could be rectangular, triangular, or another shape to accommodate first and second ancillary members 90 and 100 and a wire extending through body 20. End 45 is circular in the preferred embodiment but, end 45 can be another shape to accommodate the passage of a wire. Threading 50 is not visible from this view because of the taper of body 20. Apertures 60 are visible from the inside of body 20.

Figure 9:
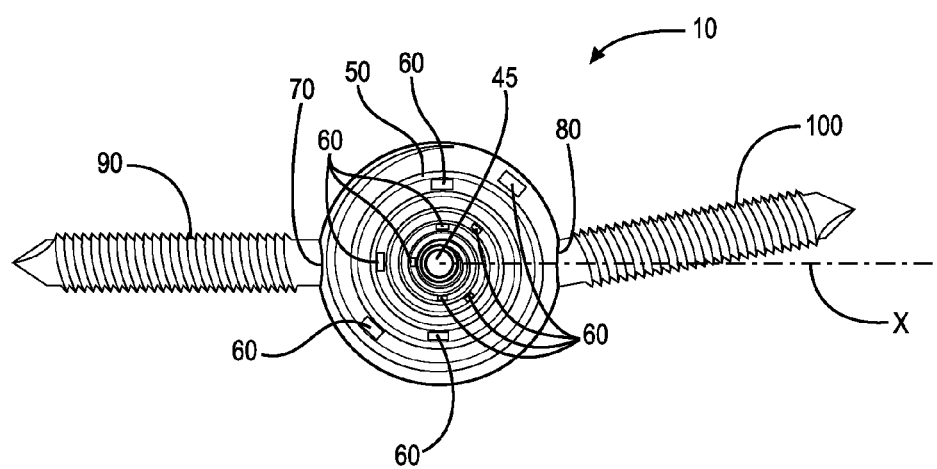
FIG. 9 is a bottom plan view of the present invention.

At the other end, FIG. 9 shows tapered end 45, threading 50, plurality of apertures 60, and ancillary members 90 and 100 of SI joint fusion device 10. The heads of first and second ancillary members 90 and 100 are resting within body 20 on the inside of first and second apertures 70 and 80, respectively, and thus, are not visible. Second ancillary member 100 is shown protruding outward from body 20 and upward in relation to horizontal line X. Horizontal line X is not part of the present invention. Instead, horizontal line X is used to illustrate that first and second ancillary members 90 and 100 can be tilted or angled within first and second apertures 70 and 80, respectively, to achieve an effective fusion.

Figure 10:
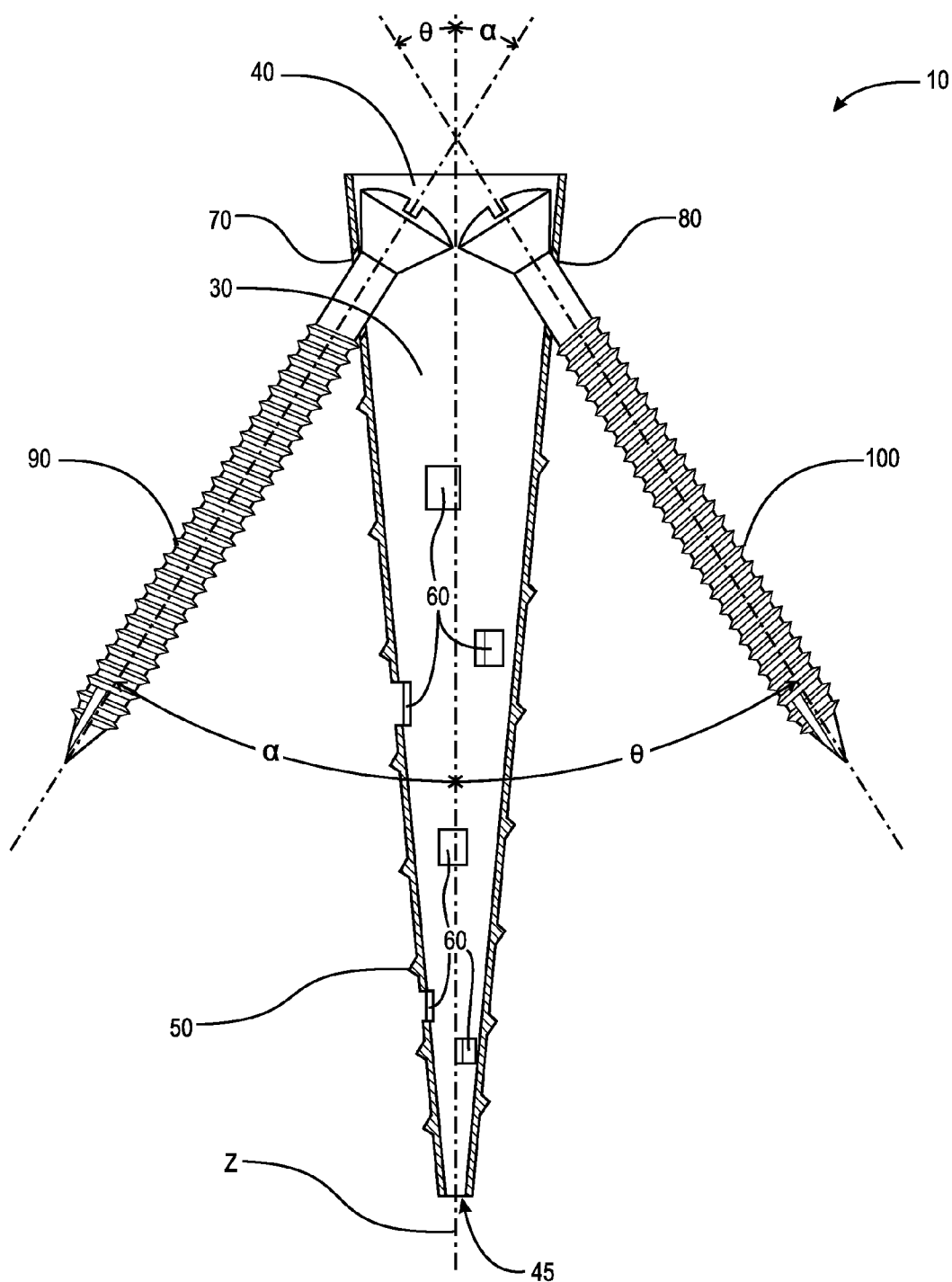
FIG. 10 is a partial cross section view of the present invention taken along line Y-Y in FIG. 8.

A partial cross-section of the present invention is shown in FIG. 10. First and second ancillary members 90 and 100 are not cut and visible as fully-intact as shown in FIG. 5. First and second ancillary members 90 and 100 are arranged at angles α and θ within first and second apertures 70 and 80, respectively, of body 20. When first and second ancillary members 90 and 100 are fully placed within first and second apertures 70 and 80, respectively, of body 20, the head portions of first and second ancillary members 90 and 100 abut the inner surface of the sidewall of body 20 and first and second apertures 70 and 80. First ancillary member 90 is operatively arranged to be inserted through end 40 and first aperture 70. Second ancillary member 100 is operatively arranged to be inserted through end 40 and second aperture 80. In an example embodiment, end 40 includes an opening defined by the frusto-conical inner surface of the sidewall of body 20. In the preferred embodiment, openings 60 are distributed equally along the length of body 20. However, it should be appreciated that plurality of openings 60 can be distributed along body 20 in any way. In the preferred embodiment, there are at least eight openings 60. From this partial cross section view, there are approximately half the number of plurality of openings 60, which are visible. It should be appreciated there could be any number of openings 60 in alternate embodiments.

Function

SI joint fusion device 10 is typically used in a minimally invasive percutaneous fusion of SI joint 16. After placing the patient in position and under anesthesia for surgery, a surgeon designates an ideal incision point and direction under image intensifier control. Then, an incision is made to access SI joint 16 and a guide wire is placed percutaneously and advanced across SI joint 16. Preferably, the incision is made along the dimple of Venus. The cartilaginous end plates of SI joint 16 are removed and a hole is drilled across SI joint 16. Then, SI joint fusion device 10 is advanced over the guide wire until it is located in SI joint 16. The ends of body 20 allow a surgeon to extend a wire, preferably a K-wire, through end 40, hollow cavity 30 of body 20, and end 45. Optionally, SI joint fusion device 10 is guided within a guide tube to protect the surrounding soft tissue. Thereafter, a surgeon removes the guide wire and drills holes under fluoroscopic guidance for placement of ancillary screw members 90 and 100 into right ilium bone 15 and sacrum 13. Once the holes are drilled, a surgeon taps and places ancillary screw members 90 and 100, respectively, into right ilium bone 15 and sacrum 13, respectively. In the preferred embodiment, ancillary screw members 90 and 100 are placed at angles $\alpha$ and $\theta$ which are as close to 80 degrees as possible in relation to vertical line Z. The greater the angle between ancillary screw members 90 and 100 and body 20, the more secure SI joint fusion device 10 is in effectively immobilizing SI joint 16. After ancillary screw members 90 and 100 are placed, respectively, hollow cavity 30 of body 20 is optionally, filled with bone graft. Preferably, a surgeon fills SI joint fusion device 10 with demineralized bone matrix, bone morphogenetic protein type 2, or autograft. Once SI joint fusion device 10 is positioned satisfactorily, the surgeon tightens ancillary screw members 90 and 100, respectively. SI joint fusion device 10 promotes the arthrodesis or fusion process.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

REFERENCE NUMERALS 10 percutaneous sacroiliac joint fusion device
12 spine
13 sacrum
14 left ilium bone
15 right ilium bone
16 sacroiliac joint
17 left femur
18 right femur
20 body
30 internal cavity
40 end
45 end
50 threading
60 plurality of openings
70 first aperture
80 second aperture
90 first ancillary member
95 first ancillary member threading
100 second ancillary member
105 second ancillary member threading
$\theta$ first angle
$\alpha$ second angle
Z central longitudinal axis
X horizontal line

What is claimed is:

1. An implantable device, comprising:
    a tapered body having a sidewall, an internal cavity, a first end, and a second end, the sidewall comprising a tapered inner surface extending between the first end and the second end, the first end including a first end opening defined by the tapered inner surface and the second end including a second end opening defined by the tapered inner surface;
    a first side opening extending through the sidewall;
    a second side opening extending through the sidewall;
    an external thread arranged about a central longitudinal axis of the tapered body;
    a first ancillary member configured to be inserted through the first opening of the first end and then through the first or second side opening; and,
    a second ancillary member configured to be inserted through the first opening of the first end and then through the first or second side opening.

2. The implantable device recited in claim 1, wherein the inner surface is frusto-conical.

3. The implantable device recited in claim 1, wherein the first side opening is arranged diametrically opposite the second side opening.

4. The implantable device recited in claim 1, wherein the external thread is helical.

5. The implantable device recited in claim 1, wherein the external thread has a continuously decreasing outer diameter along the body.

6. The implantable device recited in claim 1, further comprising a plurality of apertures to allow the passage of fusion-facilitating substances.

7. The implantable device recited in claim 1, wherein the first and second ancillary members are threaded.

8. The implantable device recited in claim 1, wherein when said first ancillary member is inserted through the first end opening and through the first or second side opening, the first ancillary member projects outwardly at a first angle $\theta$, relative to a centerline of the body, and when said second ancillary member is inserted through the first end opening and through the first or second side opening, the second ancillary member projects outwardly at a second angle $\alpha$, relative to the centerline of the body.

9. The implantable device recited in claim 8, wherein the first angle $\theta$ and the second angle $\alpha$ are both within a range of 10 to 80 degrees.

10. An implantable device, comprising:
a tapered body having a sidewall, an internal cavity, a first end, and a second end, the sidewall comprising a frusto-conical inner surface extending from the first end to the second end, the first end comprising a first end opening defined by the frusto-conical inner surface and the second end comprising a second end opening defined by the frusto-conical inner surface;
a first side opening extending through the sidewall;
a second side opening extending through the sidewall, the second side opening arranged diametrically opposite the first side opening;
an external thread arranged helically about a central longitudinal axis of the tapered body, the external thread having a continuously decreasing outer diameter along the tapered body;
a first ancillary member configured to be inserted through the first end opening and then through the first or second side opening; and,
a second ancillary member configured to be inserted through the first end opening and the through the first or second side opening.

11. The implantable device recited in claim 10, wherein said tapered body comprises a plurality of apertures to allow the passage of fusion-facilitating substances.

12. The implantable device recited in claim 10, wherein said first and second ancillary members are threaded.

13. The implantable device recited in claim 10, wherein when said first ancillary member is inserted through the first end opening and through the first or second side opening, said first ancillary member projects outwardly at a first angle θ, relative to a centerline of said tapered body, and when said second ancillary member is inserted through the first end opening and through the first or second side opening, said second ancillary member projects outwardly at a second angle α, relative to the centerline of said tapered body.

14. The implantable device recited in claim 13, wherein said first angle θ and said second angle α are both within a range of 10 degrees to 80 degrees.

15. The implantable device recited in claim 10, wherein the implantable device is made of polyetheretherketone (PEEK).

16. The implantable device recited in claim 10, wherein the implantable device is made of titanium.

17. A method for inserting and securing an implantable device into a sacroiliac joint of a person, the method comprising the following steps:
making an incision into the sacroiliac joint;
inserting a tapered body into the sacroiliac joint, the tapered body comprising:
a sidewall comprising a frusto-conical inner surface;
an internal cavity;
a first end comprising a first end opening;
a second end comprising a second end opening;
a first side opening extending through the sidewall;
a second side opening extending through the sidewall, the second side opening arranged diametrically opposite the first side opening;
an external thread arranged helically about a central longitudinal axis of the tapered body, the external thread having a continuously decreasing outer diameter along the tapered body, where the frusto-conical inner surface extends from the first end to the second end and the first end opening is defined by the frusto-conical inner surface and the second end opening is defined by the frusto-conical inner surface;
inserting a first ancillary member into and through the first end opening and then through the first side opening and securing the first ancillary member to a first bone; and,
inserting a second ancillary member into and through the first end opening and then through the second side opening and securing the second ancillary member to a second bone.

18. The method recited in claim 17, wherein the incision is made along the dimple of Venus.

19. The method recited in claim 17, wherein the body is inserted via a K-wire.

* * * * *